US006434248B1

(12) United States Patent
Juneau et al.

(10) Patent No.: US 6,434,248 B1
(45) Date of Patent: Aug. 13, 2002

(54) SOFT HEARING AID MOULDING APPARATUS

(75) Inventors: Roger P. Juneau, Destrehan; Lynn P. Creel, Kenner; Edward J. Desporte, Covington; Michael Major; Gregory R. Siegle, both of Kenner; Kelly M. Kinler, Luling, all of LA (US)

(73) Assignee: Softear Technologies, L.L.C., Harahan, LA (US)

( * ) Notice: Subject to any disclaimer, the term of this patent is extended or adjusted under 35 U.S.C. 154(b) by 0 days.

(21) Appl. No.: 09/181,843

(22) Filed: Oct. 28, 1998

Related U.S. Application Data

(63) Continuation-in-part of application No. 09/084,864, filed on May 26, 1998, now Pat. No. 6,022,311.
(60) Provisional application No. 60/068,035, filed on Dec. 18, 1997.

(51) Int. Cl.[7] .............................................. H04R 25/00
(52) U.S. Cl. ....................................... 381/322; 381/328
(58) Field of Search ................................. 381/322, 324, 381/328, 23.1; 181/129, 135, 137

(56) References Cited

U.S. PATENT DOCUMENTS

| | | | |
|---|---|---|---|
| 3,345,737 A | 10/1967 | Gordon ....................... 381/328 |
| 4,051,330 A | 9/1977 | Cole |
| 4,375,016 A | 2/1983 | Harada |
| 4,569,812 A | 2/1986 | Werwath et al. ............. 264/222 |
| 4,607,720 A | 8/1986 | Hardt |
| 4,716,985 A | 1/1988 | Haertl |
| 4,811,402 A | 3/1989 | Ward |
| 4,834,927 A | 5/1989 | Birkholz et al. ............. 264/134 |
| 4,860,362 A | 8/1989 | Tweedle ...................... 381/322 |
| 4,870,688 A | 9/1989 | Voroba et al. |
| 4,871,502 A | 10/1989 | Lebisch et al. ............. 264/222 |
| 4,880,076 A | 11/1989 | Ahlberg et al. |
| 4,937,876 A | 6/1990 | Biërmans |
| 5,002,151 A | 3/1991 | Oliveira et al. |
| 5,008,058 A | 4/1991 | Henneberger et al. ...... 264/222 |
| 5,068,902 A | 11/1991 | Ward |
| 5,185,802 A | 2/1993 | Stanton |
| 5,201,007 A | 4/1993 | Ward et al. |
| 5,259,032 A | 11/1993 | Perkins et al. |
| 5,319,163 A | 6/1994 | Scott .......................... 181/130 |
| 5,357,786 A | 10/1994 | Lung ............................. 73/81 |
| 5,430,801 A | 7/1995 | Hill |
| 5,500,902 A | 3/1996 | Stockham, Jr. et al. |
| 5,530,763 A | * 6/1996 | Aebi et al. ..................... 381/69 |
| 5,659,621 A | 8/1997 | Newton |
| 5,748,743 A | 5/1998 | Weeks ........................ 381/68.6 |
| 6,022,311 A | * 2/2000 | Juneau et al. ................. 600/25 |
| 6,052,473 A | * 4/2000 | Clavadetscher et al. .... 381/322 |

FOREIGN PATENT DOCUMENTS

| | | |
|---|---|---|
| JP | 61-238198 | 10/1986 |
| WO | WO93/25053 | 12/1993 |

OTHER PUBLICATIONS

Oliveira, Robert J., "The Active Ear", *Journal of American Academy of Audiology*, Dec. 1997, pp. 401–410.

Staab, Wayne J. and Barry Finlay, "A fitting rationale for deep fitting canal hearing instruments", *Hearing Instruments*, vol. 42, No. 1, 1991, pp. 7–10, 48.

* cited by examiner

*Primary Examiner*—Sinh Tran
(74) *Attorney, Agent, or Firm*—Garvey, Smith, Nehrbass & Doody, L.L.C.

(57) ABSTRACT

A hearing aid instrument of the in-the-ear type (and preferably CIC) provides a plate member with electronic hearing aid components mounted thereto. The plate member is preferably of a harder material such as hard plastic. A soft polymeric body is bonded to the plate member and encapsulates preferably a plurality of the electronic hearing aid components. The body is soft and is shaped to conform to the ear canal of the user. The soft polymeric body and encapsulated electronic hearing aid components define a soft structure compliant to the ear canal during use and that is substantially solid and free of void spaces between at least some of the components and the ear canal. This combination of soft compliant structure and encapsulated electronic hearing aid components addresses problems of peripheral leakage, poor fit, pivotal displacement that occurs with jaw motion and internal cross talk of components housed in prior art hollow type hearing aids.

23 Claims, 8 Drawing Sheets

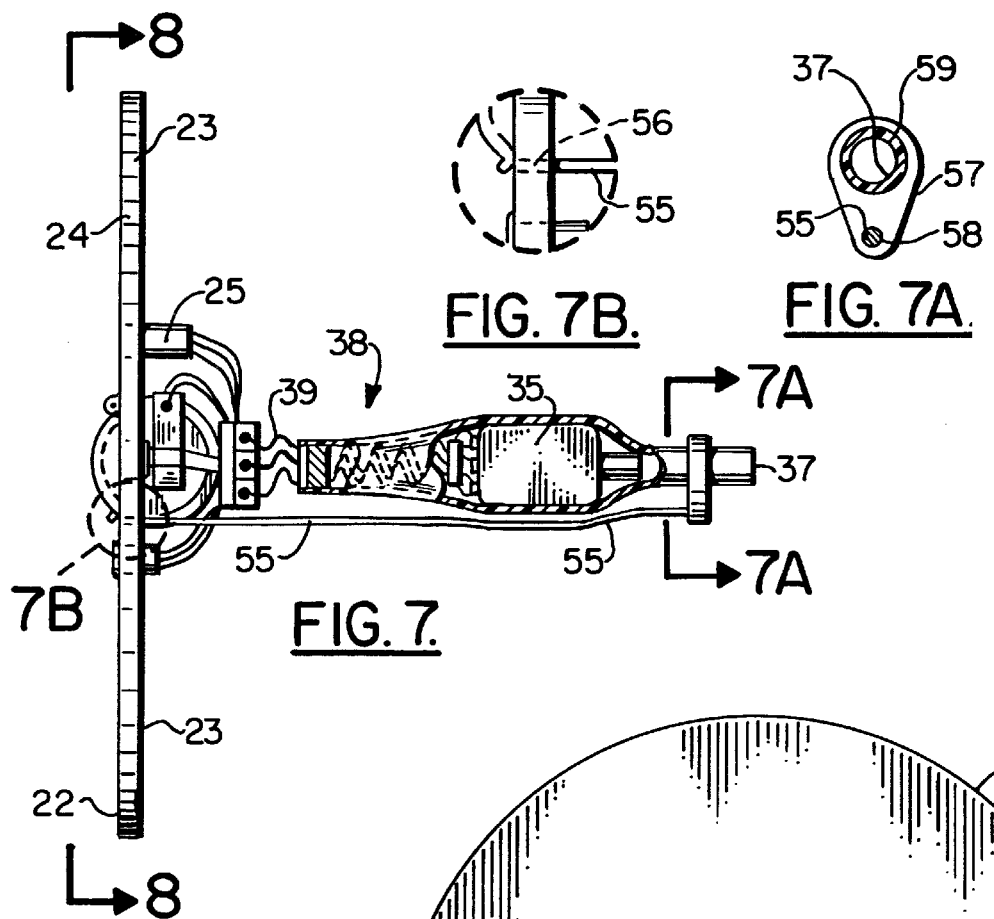
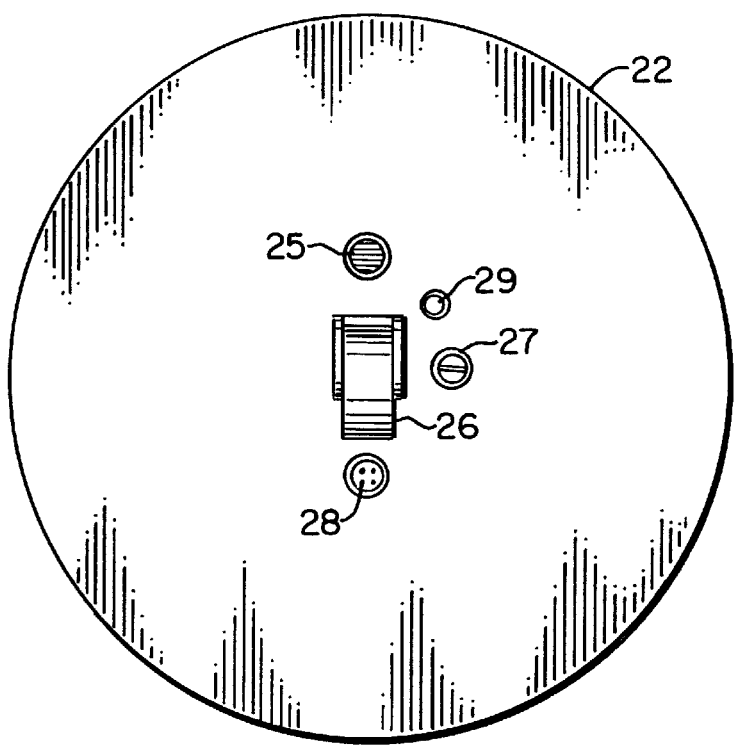

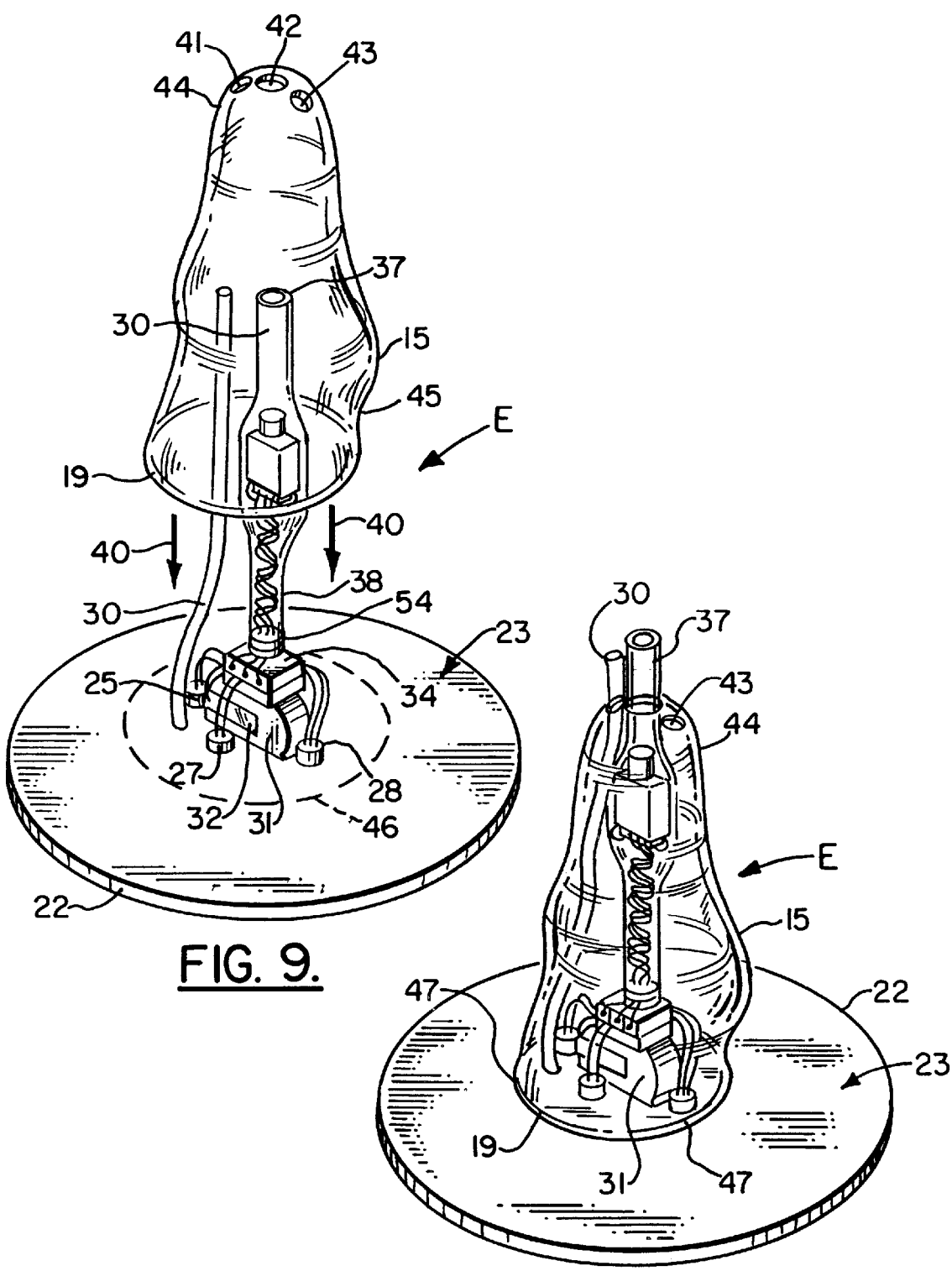

SOFT HEARING AID MOULDING APPARATUS

CROSS-REFERENCE TO RELATED APPLICATIONS

This is a continuation-in-part of our U.S. patent application Ser. No. 09/084,864, filed May 26, 1998 now U.S. Pat. No. 6,022,311, and incorporated herein by reference.

Priority of U.S. Provisional Patent Application Ser. No. 60/068,035, filed Dec. 18, 1997, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to hearing aids and more particularly to an improved hearing aid, its method of manufacture and an improved method of compensating for hearing loss. More particularly, the present invention provides an improved method and apparatus for compensating for hearing loss that uses a construction combining a rigid mounting member (for example, a face plate) with a soft polymeric body that is joined to the mounting member and which encapsulates some of the electronic hearing aid components of the apparatus, the soft polymeric body being sized and shaped to conform to the user's ear canal during use. It may be possible to use a soft polymeric material as the face plate.

2. General Background of the Invention

The hearing industry has realized major strides in the development of high-fidelity, high-performance products, the most recent of which is digital signal processing technology. Hearing care professionals expected those advancements to solve the shortcomings of traditional amplification, and to push the market forward. Those expectations have not been fully realized. While these developments have solved many of the problems associated with traditional electronic design and steadily gained market share, they have not fostered overall market growth.

The issues of early acoustic feedback, less than optimum fidelity and intermodulation of the frequency response cannot be completely resolved by electronic manipulation of the signal by either analog or digital means.

Historically, custom-molded ear worn hearing instruments have been limited to an "acrylic pour" process as the means of the construction. With the advent of miniaturization and technological advancement of computer chip programming, the ear-worn instruments have become smaller and are positioned into the bony portion of the ear canal, commonly referred to as "deep insertion technology".

Developments outside the hearing industry have culminated in a new level of micro-miniaturization of electronic components for industry applications. Consequently, advanced signal processing can be housed in less space than was required for traditional electro-acoustic components.

With the development of programmable hearing aids, using either analog or digital signal processing, custom electronic design has shifted from the manufacturing level to the clinical level. The clinician can now customize the electro-acoustic response via software. It is no longer necessary for the device to be returned to the manufacturer for hardware changes to arrive at the desired electro-acoustic response. However, it is still often necessary to return the device for shell modifications.

In direct contrast to electronic advances within the industry, little or no advancement has been realized in custom prosthetic design. Since the late 1960's, when the custom in-the-ear hearing aid was developed, materials and construction techniques remained virtually unchanged. These materials and techniques were adopted from the dental industry, whereby the customized housing-commonly called a "shell" was constructed using acrylic of 90 point Durometer Hardness Shore D. This construction process provided the structure and the strength of material necessary to protect the electronics.

At the time the acrylic shell was developed, hearing instruments were worn in the relatively forgiving cartilaginous portion of the ear canal. Micro-miniaturization of electronic components, combined with increased consumer demand for a cosmetically acceptable device, has shifted the placement of the hearing aid toward the bony portion of the ear canal.

The bony portion of the canal is extremely sensitive and intolerant of an acrylic shell when that shell is over sized due to standard waxing procedures or is in contact with the canal wall beyond the second anatomical bend. Rigid acrylic that does not compress must pivot in reaction to jaw or head movement, thereby changing the direction of the receiver yielding a distorted acoustic response. In addition, the pivot action causes displacement of the device resulting in unwanted acoustic feedback. This problem has necessitated countless shell modifications, thereby compromising the precision approach of the original dental technology. Many such devices require some modification by the manufacturer. Most manufacturers can expect a high percentage of returns for modification or repair within the first year. Consequently, CIC (completely in canal) shell design has been reduced to more of a craft than a science. Although the recent introduction of the ultra-violet curing process has produced a stronger, thinner shell, the overall Shore Hardness remained unchanged.

The current trend for custom hearing aid placement is to position the instrument toward the bony portion of the ear canal. The ear canal can be defined as the area extending from the concha to the tympanic membrane. It is important to note that the structure of this canal consists of elastic cartilage laterally, and porous bone medially. The cartilaginous portion constitutes the outer one third of the ear canal. The medial two-thirds of the ear canal is osseous or bony. The skin of the osseous canal, measuring only about 0.2 mm in thickness, is much thinner than that of the cartilaginous canal, which is 0.5 to 1 mm in thickness. The difference in thickness directly corresponds to the presence of apocrine (ceruminous) and sebaceous glands found only in the fibrocartilaginous area of the canal. Thus, this thin-skinned thinly-lined area of the bony canal is extremely sensitive to any hard foreign body, such as an acrylic hearing instrument.

Exacerbating the issue of placement of a hard foreign body into the osseous area of the ear canal is the ear canal's dynamic nature. It is geometrically altered by temporomandibular joint action and by changes in head position. This causes elliptical elongation (widening) of the ear canal. These alterations in canal shape vary widely from person to person. Canal motion makes it very difficult to achieve a comfortable, true acoustic seal with hard acrylic material. When the instrument is displaced by mandibular motion, a leakage or "slit leak" creates an open loop between the receiver and the microphone and relates directly to an electroacoustic distortion commonly known as feedback. Peripheral acoustic leakage is a complex resonator made up of many transient resonant cavities. These cavities are transient because they change with jaw motion as a function of time, resulting in impedance changes in the ear canal. These transients compromise the electroacoustic performance.

The properties of hard acrylic have limitations that require modification to the hard shell exterior to accommodate anatomical variants and the dynamic nature of the ear canal. The shell must be buffed and polished until comfort is acceptable. The peripheral acoustic leakage caused by these modifications results in acoustic feedback before sufficient amplification can be attained.

Hollow shells used in today's hearing aid designs create internal or mechanical feedback pathways unique to each device. The resulting feedback requires electronic modifications to "tweak" the product to a compromised performance or a "pseudo-perfection". With the industry's efforts to facilitate the fine-tuning of hearing instruments for desired acoustic performance, programmable devices were developed. The intent was to reduce the degree of compromise, but by their improved frequency spectrum the incidence of feedback was heightened. As a result, the industry still falls well short of an audiological optimum.

A few manufacturers have attempted all-soft, hollow shells as alternatives to acrylic, hollow shells. Unfortunately, soft vinyl materials shrink, discolor, and harden after a relatively short period of wear. Polyurethane has proven to provide a better acoustic seal than polyvinyl, but has an even shorter wear life (approximately three months). Silicones have a long wear life but are difficult to bond with plastics such as acrylic, a necessary process for the construction of custom hearing instruments. To date, acrylic has proven to be the only material with long term structural integrity. The fact remains, however, that the entire ear is a dynamic acoustic environment and is ill-served by a rigid material such as acrylic. Also, the acrylic hearing aids typically need to be returned to the manufacturer for major shell modifications.

The following references are all incorporated herein by reference:

U.S. Pat. Nos.: 4,051,330; 4,375,016; 4,607,720; 4,716,985; 4,811,402; 4,870,688; 4,880,076; 4,937,876; 5,002,151; 5,068,902; 5,185,802; 5,201,007; 5,259,032; 5,530,763; 5,430,801; 5,500,902; and 5,659,621.

Also of interest and incorporated herein by reference are published Japanese patent application no. JA61-238198, the articles from December 1997 Journal of American Academy of Audiology, and Staab, Wayne J. and Barry Finlay, "A fitting rationale for deep fitting canal hearing instruments", Hearing Instruments, Vol. 42, No. 1, 1991, pp. 7–10, 48.

BRIEF SUMMARY OF THE INVENTION

The present invention provides a method and material for the construction of a soft hearing instrument that is solid (i.e. eliminates void spaces). This instrument includes a soft body portion that is truly soft, comprising an elastomer of about 3 to 55 durometer Shore A and preferably 10–35 durometer Shore A. This product is unique in that it is solid, with the electronic components actually encapsulated or embedded within the soft fill material. The fill material can be a Dow Corning® MDX-4-4210 silicone or a silicone polymer distributed by Factor II, Inc. of Lakeside, Ariz., designated as product name 588A, 588B, 588V.

The present invention provides a method that can replace traditional acrylic shell construction. Unlike the shell construction process, the ear impression is not modified, built up, or waxed. With the elimination of these steps, a more faithful reproduction of the ear impression is accomplished. With the present invention, the manufacturer should be able to produce a hearing aid body which will not need to be returned as frequently for modification as with present hard acrylic hearing aid bodies.

The apparatus of the present invention is virtually impervious to the discoloration, cracking, and hardening experienced with polyvinyls and polyurethanes.

The hearing aid of the present invention provides a greater range of gain before feedback occurs.

The outer surface of the body of the present invention is preferably non-absorbent and virtually impervious to cerumen.

As used herein, "in the ear hearing aids" includes all hearing aids which have all of the electronics positioned in the ear, and thus includes hearing aid styles ranging from full concha to CIC (completely in the canal) hearing aid styles.

The preferred embodiment of the present invention shown in the drawings is a CIC hearing aid style.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 7 is a partial elevational view of the preferred embodiment of the apparatus of the present invention illustrating the mounting member and the plurality of the electronic hearing aid components;

FIG. 7A is a cross-sectional view taken along the line 7A—7A in FIG. 7;

FIG. 7B is a partial view showing the portion indicated in FIG. 7 as 7B;

FIG. 8 is a elevational view of the lateral side of the mounting member taken along lines 8—8 of FIG. 7;

FIG. 9 is a perspective view illustrating the method step of joining the female mould to the mounting member at the medial side thereof;

FIG. 10 is a perspective view of the preferred embodiment of the apparatus of the present invention and showing the method of the present invention after the joining of the female mould and mounting member;

DETAILED DESCRIPTION OF THE INVENTION

Figure 1:
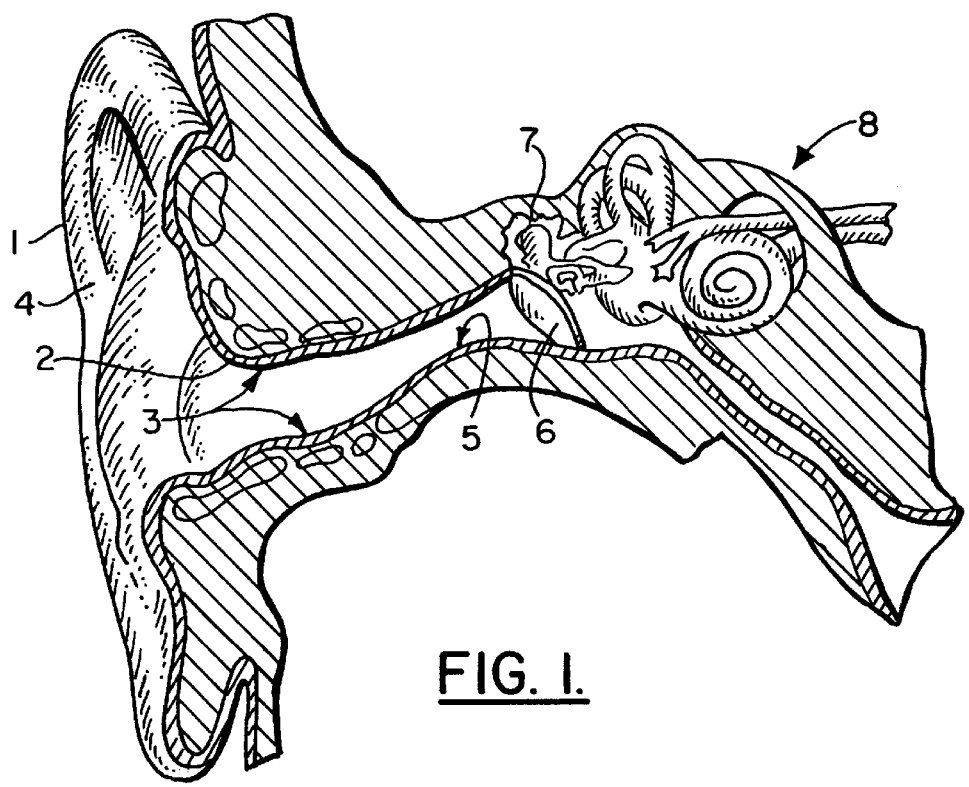
FIG. 1 is a sectional elevational view of a user's hearing area to show the anatomy thereof.
Figure 2:
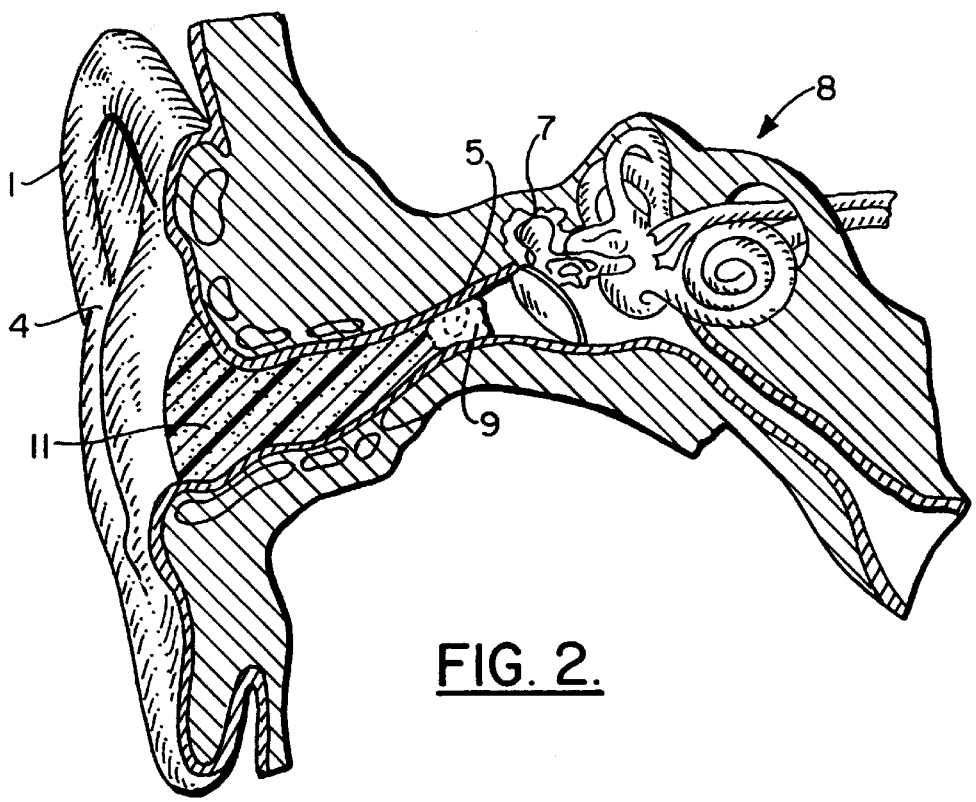
FIG. 2 is a sectional elevational view of a user's ear canal showing placement of a dam and mold material as part of the method of the present invention.

FIGS. 1 and 2 show a user's ear 1 and anatomical parts of the ear. In FIG. 1 there can be seen the external auditory canal 2, ear canal wall 3, auricle 4, isthmus 5, tympanic membrane 6, middle ear 7 and inner ear 8. In FIG. 2 a dam 9 such as a cotton dam or Otoblock® dam is positioned at the isthmus 5. The dam 9 is used as a first step of the method of the present invention wherein a form portion 11 or impression material is formed of silicone, methylmethacrylate or algenate. The form 11 is formed in between dam 9 and auricle 4 as shown in FIG. 2.

Figure 3:
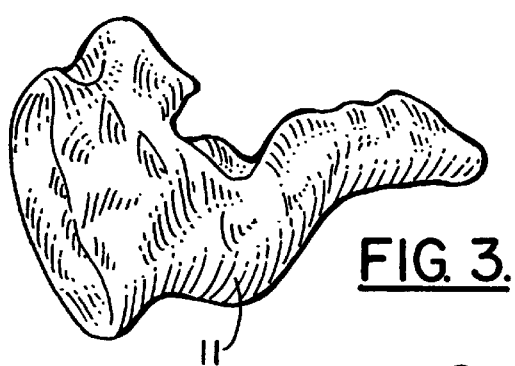
FIG. 3 is a perspective view of the form portion used with the preferred method of the present invention.
Figure 4:
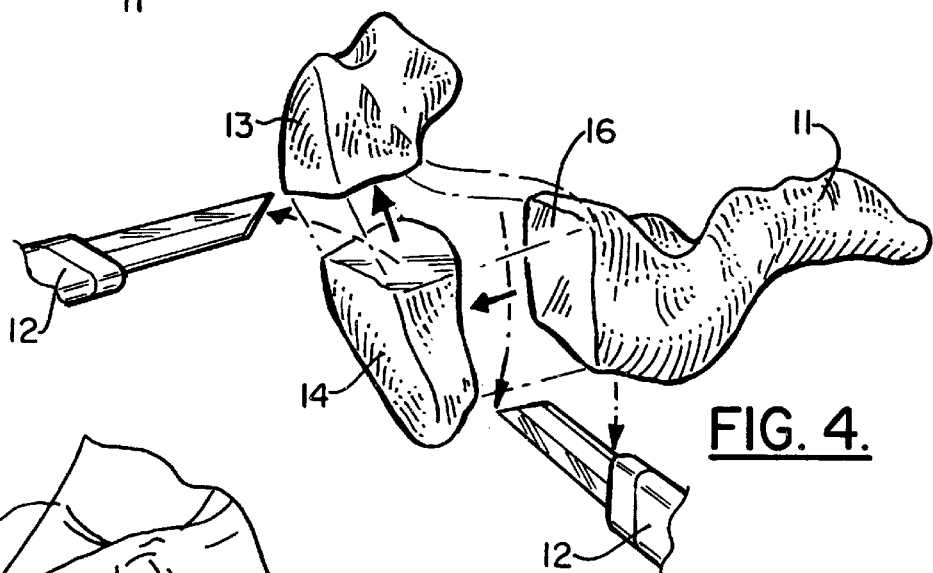
FIG. 4 is a perspective view illustrating shaping of the form as part of the method of the present invention.
Figure 5:
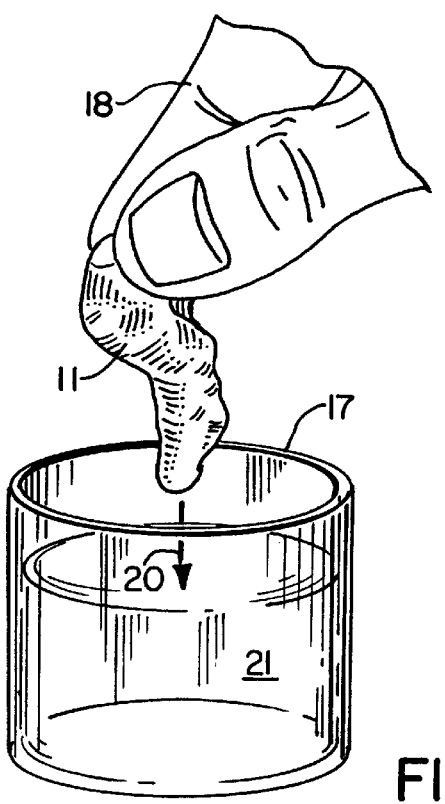
FIG. 5 is a perspective view illustrating a dipping of the form into a vessel carrying material for making the female mould as part of the method of the present invention.

During the method step of making the form 11, the form 11 conforms to all of the curvatures of the ear canal 3 so that an accurate form 11 is provided for making a female mould. 4 The female mould 15 is shown in FIGS. 5, 6 and 9–12. In FIGS. 3 and 4, the form 11 is shown after being removed from the ear 1 (FIG. 3) and during a cutting of the form 11 using knives 12 to cut excess material that is designated as 13, 14 in FIG. 4. The form 11 is separated from excess material 13 and 14 at sagittal plane 16. After the form 11 is trimmed in FIG. 4, a technician's hand 18 dips the form 11 into vessel 17 as schematically indicated by the arrow 20. The vessel 17 includes a liquid material 21 that cures at room temperature such as room temperature curing methacrylate (sold by Esschem). It is preferable to use a clear material 21 in the method step shown in FIG. 5.

Figure 6:
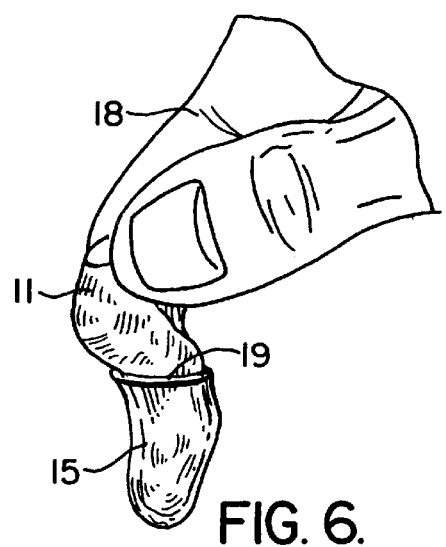
FIG. 6 is a perspective view illustrating a coating of the form with the female mould as part of the method of the present invention.

In FIG. 6, the technician's hand 18 has removed the form 11 so that a coating of material 21 cures at room temperature (or with an ultraviolet light process) to form female mould 15 on 30 form 11. After it cures, the female mould 15 is removed from form 11 for use as shown in FIGS. 9 and 10 during assembly of the apparatus 10 of the present invention. The mould 15 can be a few millimeters in wall thickness (typically 1–3 mm). A number of electronic components are mounted to a mounting member 22 prior to use of the female mould 15. Mounting member 22 provides a medial side 23 and lateral side 24. The medial side 23 supports a number of hearing aid electronic components as shown in FIGS. 7, 9, and 10. In FIG. 7, these hearing aid electronic components include commercially available hearing aid components including a microphone 25, volume control, battery, socket or plug 28 for communicating with a computer, chip or micro processor circuit, wiring harness 38, input capacitor, amplifier 34, receiver/speaker 35, and receiver tube 37.

Figure 15:
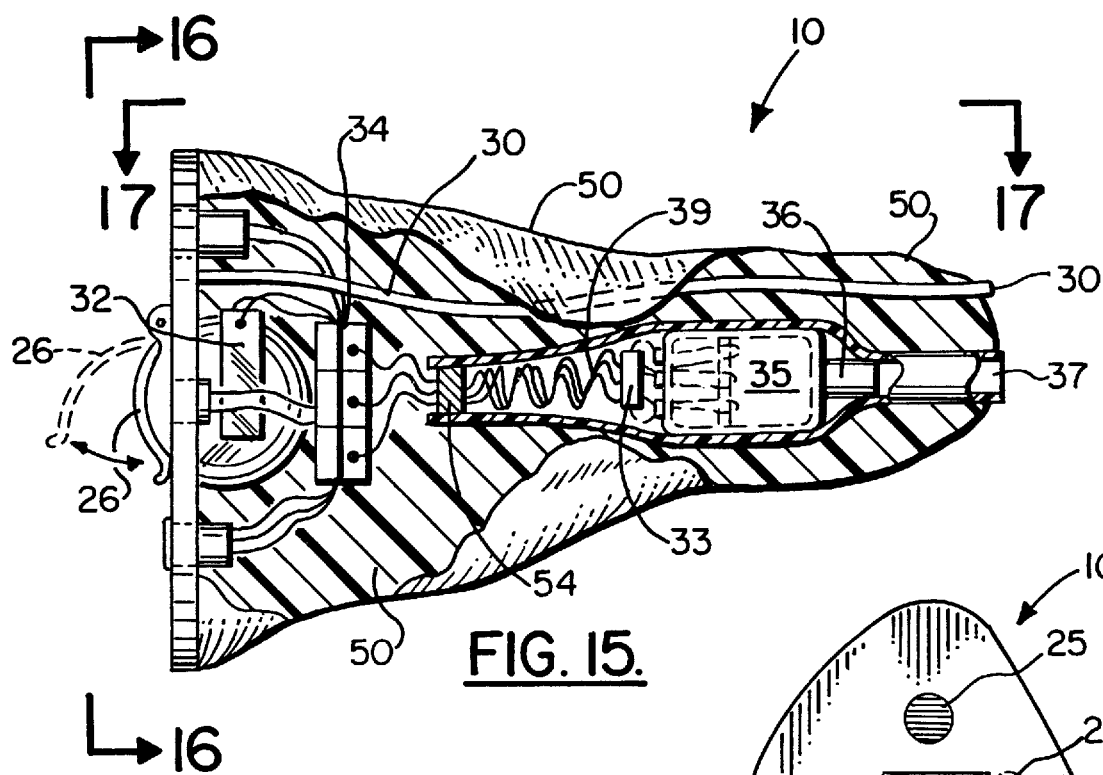
FIG. 15 is an elevational view of the preferred embodiment of the apparatus of the present invention.
Figure 16:
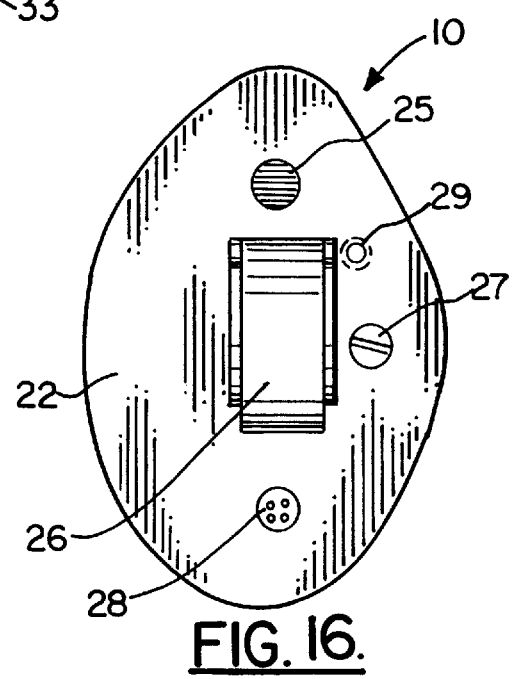
FIG. 16 is an end view of the preferred embodiment of the apparatus of the present invention taken along lines 16—16 of FIG. 15.
Figure 17:
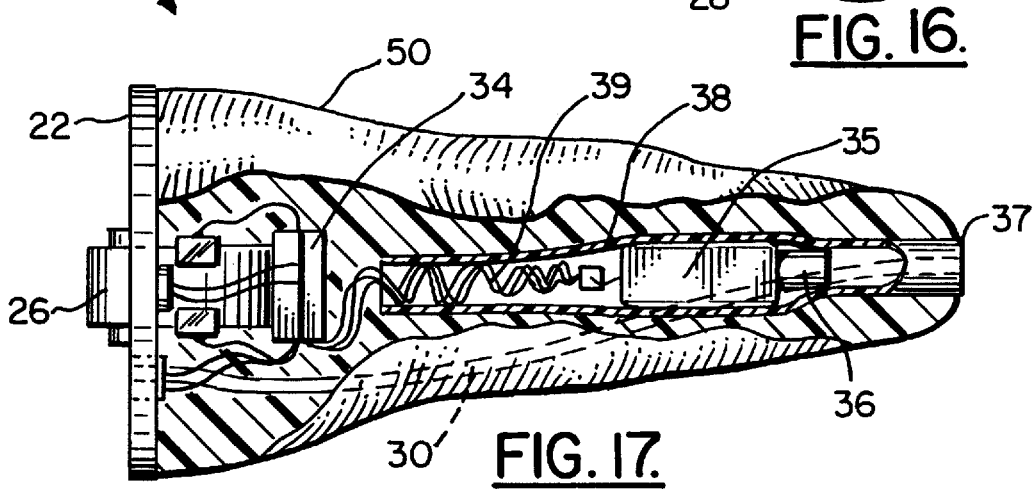
FIG. 17 is a top view of the preferred embodiment of the apparatus of the present invention taken along lines 17—17 of FIG. 15.

In FIG. 8, the lateral side 24 of mounting member 22 shows the microphone 25, battery compartment 26, volume control 27, programming socket 28 for communicating with a computer, silicone plug 54 (see FIG. 9), and vent opening 29 that communicates with vent tube 30 (see FIG. 10). In FIG. 9, battery 31 is shown housed in battery compartment 26. The electronic hearing aid components also include a battery terminal 32, voltage regulating capacitor 33 (see FIG. 15), amplifier/microprocessor 34, receiver 35 having speaker port 36, and receiver tube 37. A wiring harness 38 includes a plurality of wires that connect to various electronic components of the hearing aid device together. The wiring harness 38 includes a length of wires 39 that are arranged in an S or multiple curved pattern as shown in FIG. 7. This "S loop" configuration of wires 39 helps protect the integrity of the electronics when the hearing aid apparatus 10 is flexed as occurs during use because of its soft nature. Further, the S-loop wires 39 are preferably a 44 gauge five strand Litz wire (or magnet wire). The length of the S-loop wires 39 is preferably at least 1.5 times the distance between the terminals to the receiver (or microprocessor) 35 and the amplifier 34 terminals. These "S-Loop" wires 39 prevent excess tension or compression from being transmitted to the electronics during use (e.g. flexing, elongation, compression of hearing aid 10).

Vent tube 30 is anchored to the mounting member 22 and preferably also to one of the electronic components at a position spaced away from the mounting member 22. Vent tube 30 acts as a tensile load carrying member that carries tension so that the wiring harness 38 is substantially free of a tensile load that could damage the wiring harness 38. Also, when vent tube 30 is anchored to one of the electronic components (such as receiver 35) at a position spaced away from the mounting member 22, it may provide enough strain relief that it would not be necessary to coil wires 39 as shown (they could be straight instead).

Something else could be used as a load carrying member, in place of vent tube 30 (in which case vent tube 30 would not necessarily be anchored to one of the electronic components (such as receiver 35)) at a position spaced away from the mounting member 22. For example, a monofilament cantilever 55 can be used to carry tension so that tension is not transmitted to wiring harness 38. In FIGS. 7, 7A, and 7B the link 55 is anchored to plate 22 at opening 56. Fastener 57 affixes to receiver tube 37 at large opening 59. Monofilament cantilever 55 attaches to fastener 57 at smaller diameter opening 58. Alternatively, vent tube 30 could be manufactured of a tensile material that carries tensile load. The vent tube 30 would then be anchored to plate 22 and fastener 57 as the tensile member.

The monofilament cantilever 55 provides longitudinal stability to the body. It minimizes longitudinal displacement (stretching as well as compression) and thus acts as a longitudinal stabilizer (a longitudinal load carrying member).

After the electronic components (sometimes designated generally in the drawings by the letter "E") are assembled to the medial 23 side of mounting member 22, female mould 15 is used to complete the method of construction of the present invention as shown in FIG. 9–13. In FIG. 9, the female mould 15 is placed over the electronic components "E" beginning with the distal end portion of receiver tube 37 and the distal end portion of vent tube 30 as indicated by arrows 40 in FIG. 9. A plurality of three openings 41, 42, 43 are provided at distal end 44 of female mould 15 as shown in FIG. 9. The proximal end 45 of female mould 15 provides an annular edge surface 19 that engages the medial 23 side of mounting member 22 as indicated by the dotted line 46 in FIG. 9.

A joint is formed between annular edge surface 19 of female mould 15 and medial surface 23 of mounting member 22 at a position schematically indicated as dotted line 46 in FIG. 9, using the method of the present invention. The medial surface 23 of mounting member 22 is cleaned with a suitable solvent. Acetone can be used as a solvent in the case of a mounting plate 22 that is made of acrylic. The medial surface 23 of mounting member 22 is then painted with a primer using a swab or brush. The primer is allowed to dry. A bonding agent is then applied to the medial surface 23 of mounting member 22 and allowed to dry. The bonding agent or bonding enhancer can be product A-320 of Factor II, Inc. of Lakeside, Ariz., which is a member of the chemical family "silicone primer".

The female mould 15 is placed against the medial side 23 of mounting member 22. A liquid acrylic is used to form an acrylic seam at the interface of annular edge surface 19 of female mould 15 and the medial side 23 of mounting member 22 (see FIG. 10). As the female mould 15 is assembled to mounting member 22, vent tube 30 passes through opening 41. Receiver tube 37 passes through opening 42. The opening 43 is then used for injection of filler material 50 (e.g. via needle 49) as shown by arrows 51, 52 in FIG. 11. During this process, temporary seal 47 holds the liquid filler material 50 within the interior 53 that is formed by female mould 15 and mounting member 22. The filler material 50 can be a liquid during the injection step of FIG. 11 so that it encapsulates at least the receiver/speaker electronic component 35 and preferably other components as well.

Figures 11, 12, 13, 14:
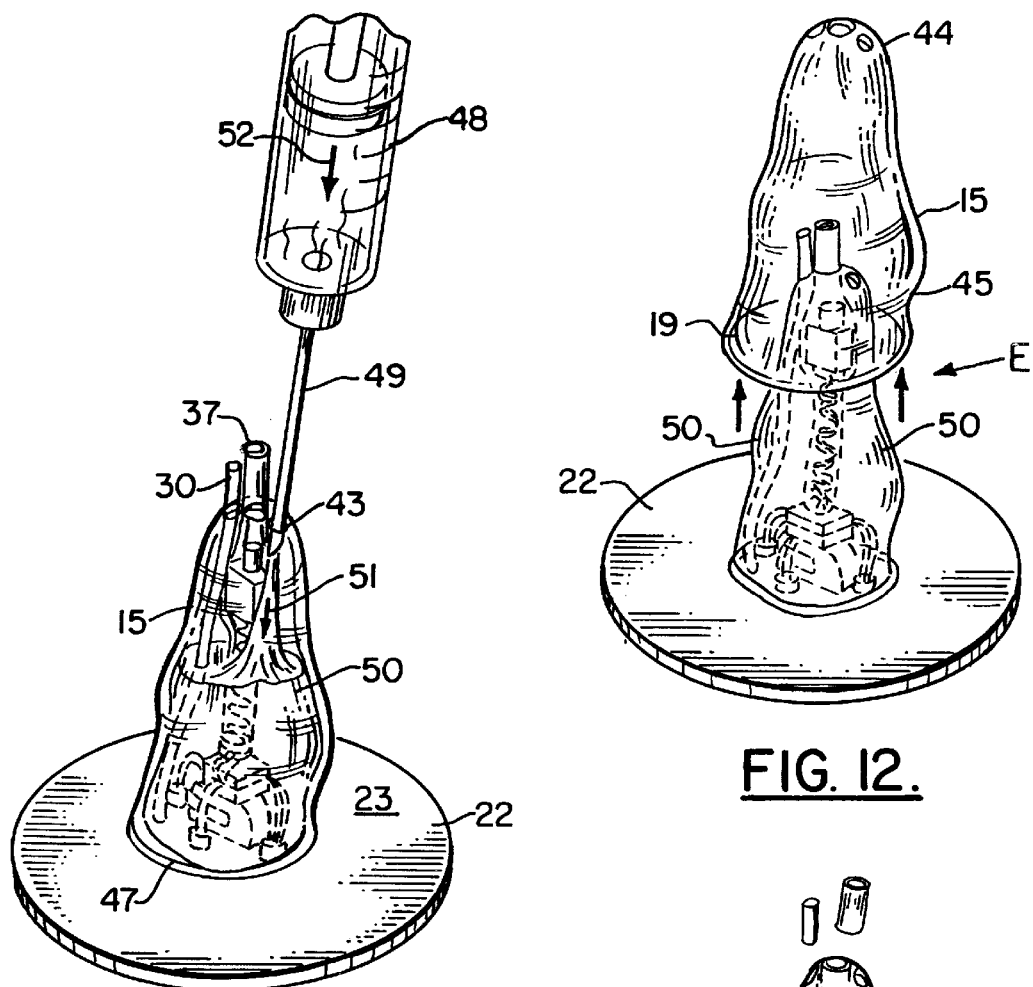
FIG. 11 is a perspective view illustrating the method step of adding filler material to the interior of the female mould and encapsulating electronic hearing aid component portions of the apparatus.
FIG. 12 is a perspective view illustrating removal of the female mould after the filler material has set and encapsulating the electronic hearing aid components.
FIG. 13 is a perspective of the preferred embodiment of the apparatus of the present invention and the method of the present invention illustrating removal of excess plate and tube material from the mounting member.
FIG. 14 is a perspective view of the preferred embodiment of the apparatus of the present invention.

In FIG. 12, the female mould 15 is removed after the material 50 has set. The mounting member 22 (which can be in the form of a circular, generally flat face plate) is then cut at the phantom line 46 that basically tracks the periphery of female mould 15 at annular edge surface 19 at proximal end 45 thereof.

This cutting of the unused, unneeded part of mounting member 22 is shown in FIG. 13. FIGS. 14–17 show the completed apparatus 10 of the present invention.

The present invention provides a soft, yet solid hearing aid instrument that will provide a more appropriate environment for both the high fidelity performance of today's advanced circuitry and the dynamic ear canal.

The present invention teaches a soft construction of at least the distal portion of the apparatus 10 so that at least the receiver/speaker is encapsulated with the soft material 50. This construction results in a precise representation of the human ear canal, flex with jaw motion, and cushion for the embedded electronic components "E".

Figure 18:
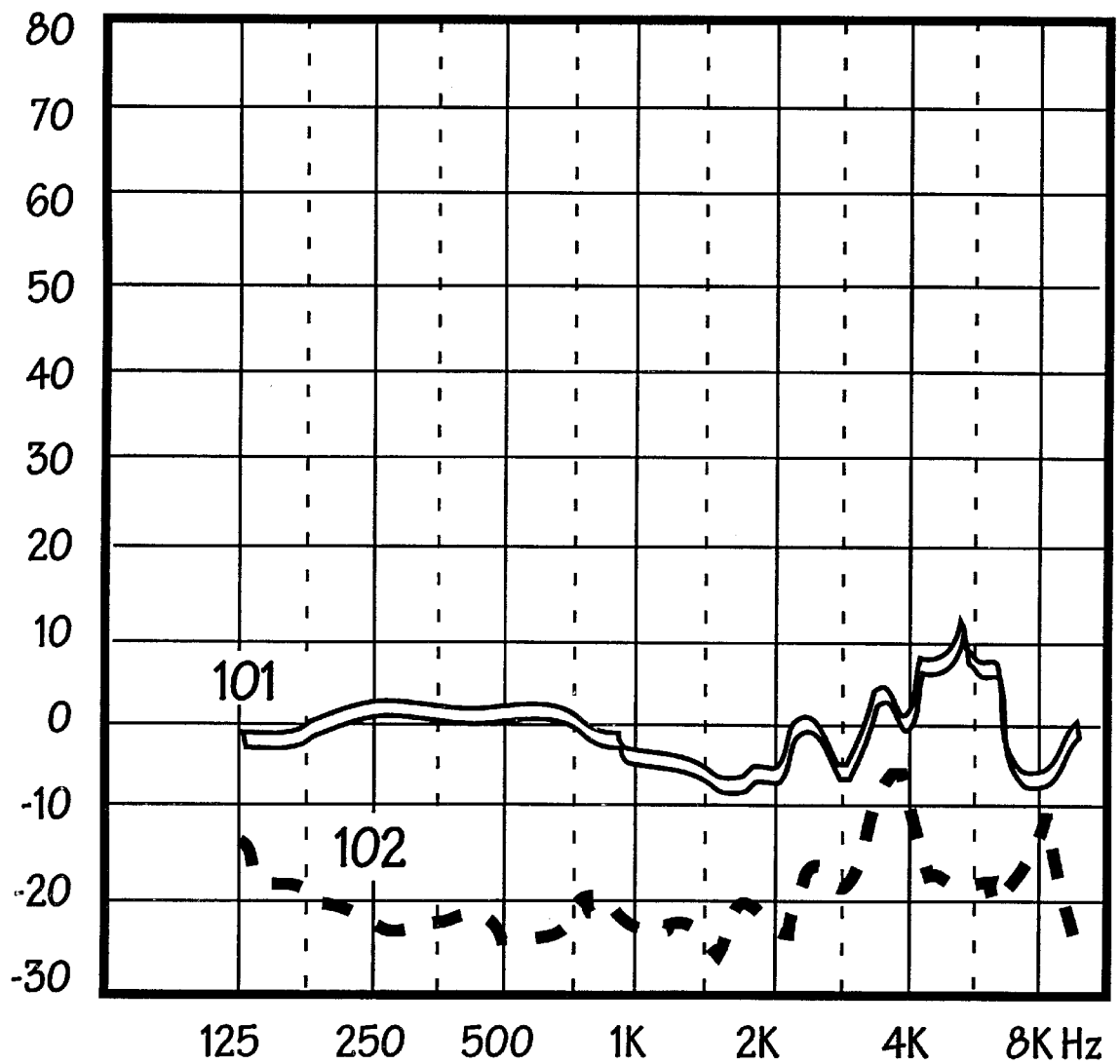
FIG. 18 is a graphical representation of a comparison of real ear occlusion gain for the present invention versus a hard shell, hollow-type instrument.

FIG. 18 demonstrates real ear occlusion gain (REOG) finding obtained from a wearer having a tortuous ear canal. The curve 101 represents the REOG of a hard shell, hollow type hearing aid instrument. The curve 102 represents the REOG of an instrument 10 made according to the method of the present invention. As can be seen in FIG. 18, the present invention instrument provided 20 dB more attenuation than did the hard shell, hallow hearing aid instrument represented by the curve 101. Because of the sharp first directional bend of the wearer's ear canal, the hard shell instrument could not be inserted without modification. The apparatus 10 of the present invention was insertable without modification thereby yielding a tighter seal in the wearer's ear.

Figure 19:
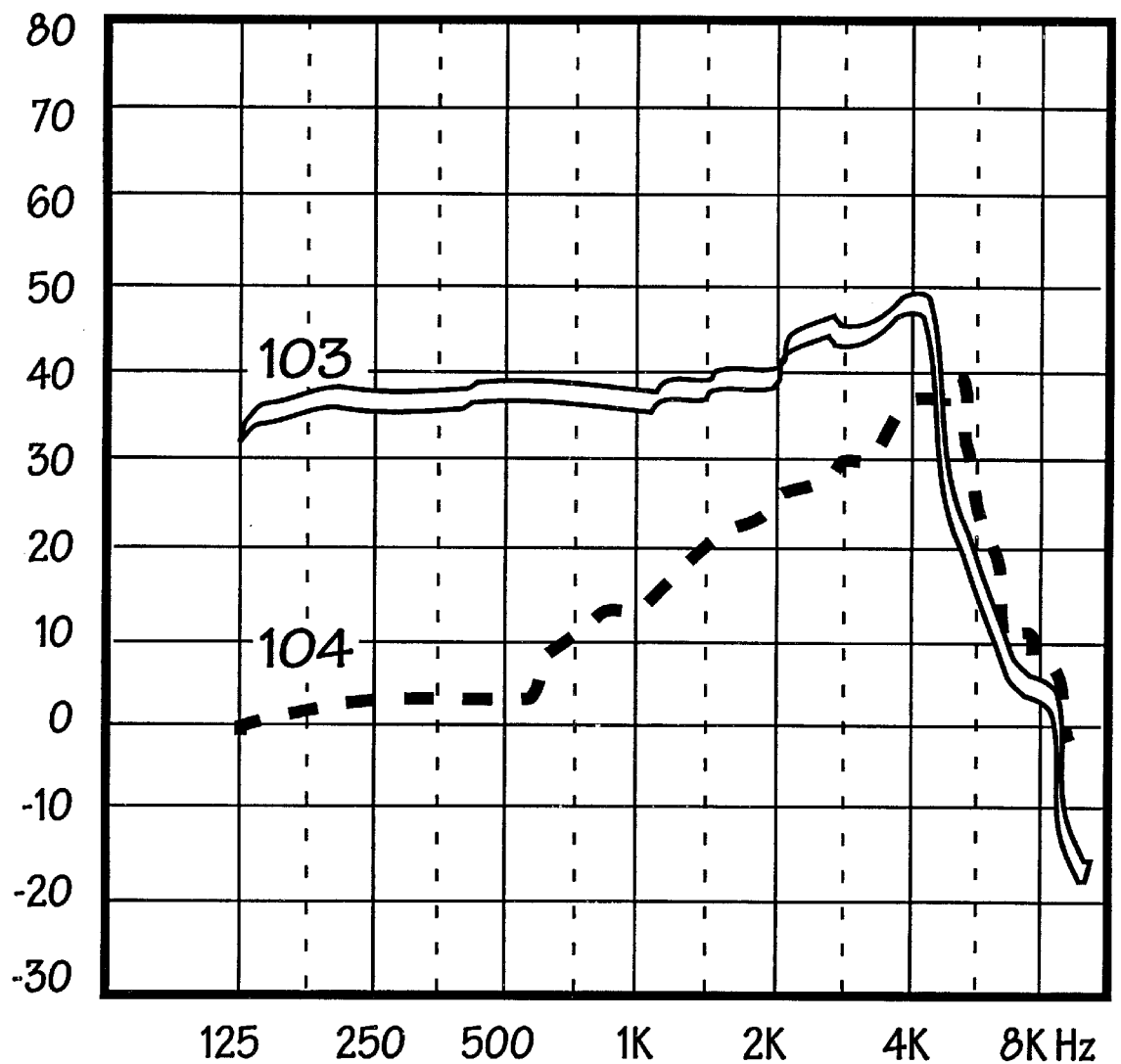
FIG. 19 is a graphical representation showing a comparison of real ear aided gain obtained before acoustic feedback, comparing the present invention with a hard shell, hollow-type instrument.

FIG. 19 is a graphical representation that demonstrates real ear aided gain (REAG) findings obtained from a wearer having a tortuous ear canal. The curves shown (103, 104) were obtained from the instruments used to generate the finding shown in FIG. 18. Curve 103 represent REAG before feedback of the apparatus 10 of the present invention. Curve 104 demonstrates the REAG before feedback of a hard shell, hollow type hearing aid instrument of the prior art. As can be seen in FIG. 19, the instrument 10 of the present invention represented by curve 103 provided more gain across the frequencies. This REAG is inversely proportional to the amount of occlusion gain (REOG) or attenuation provided by the apparatus 10 of the present invention. It should be restated that, because of the sharp first directional bend of the wearer's ear canal, the hard shell, hollow type instrument of the prior art could not be inserted without being modified. The apparatus of the present invention was insertable without modification, thus the present invention provides higher added gain values (REAG) when a more negative REOG can be achieved while maintaining comfort.

The apparatus 10 of the present invention will result in a better utilization of advanced circuitry and a more comfortable hearing instrument. The soft construction solves the problem of peripheral leakage, poor fit, and pivotal displacement that often occurs with jaw motion. Another problem that is solved with the present invention is the elimination of internal cross-talk of components housed in hollow shell type hearing aids.

The following table lists the parts numbers and parts description as used herein and in the drawings attached hereto.

Parts List

Part Number Description
1 ear
2 external auditory canal
3 ear canal wall
4 auricle
5 isthmus
6 tympanic membrane
7 middle ear
8 inner ear
9 dam
10 hearing aid
11 form
12 knife
13 excess material
14 excess material
15 female mold
16 sagittal plane
17 vessel
18 technician's fingers
19 annular surface
20 arrow
21 mold material
22 mounting member
23 medial side
24 lateral side 25 microphone
26 battery compartment
27 volume control
28 programming socket
29 vent opening
30 vent tube
31 battery
32 battery terminal
33 voltage regulating capacitor
34 amplifier/microprocessor
35 receiver
36 receiver port
37 receiver tube
38 wiring harness
39 s-loop wires
40 arrow
41 opening
42 opening
43 opening
44 distal end
45 proximal end
46 dotted line
47 temporary seal
48 syringe
49 needle
50 filler material
51 arrow
52 arrow
53 interior space
54 silicone plug
55 monofilament cantilever
56 opening
57 fastener
58 small opening
59 large opening The foregoing embodiments are presented by way of example only; the scope of the present invention is to be limited only by the following claims.

What is claimed is:

1. A hearing aid molding apparatus for constructing a hearing aid that is to be contained in a user's ear during use, comprising:
   a) a mounting member providing a support for holding one or more electronic hearing aid components mounted thereto;
   b) a soft polymeric hollow outer shell that is only temporarily joined to the mounting member, the outer shell and mounting member defining a mold cavity that contains a plurality of electronic hearing aid components and that can be filled with a soft polymeric filler material;
   c) the soft polymeric filler substantially fills the mold cavity, the outer shell being removable from the soft polymeric filler to form a soft polymeric body that engages the inner respective surfaces of the mounting member to thereby minimize the volume of void space and encapsulate the electronic hearing aid components, the soft polymeric body having an inner surface shaped to conform to and that contacts the ear canal of a user;
   d) the soft polymeric body and the encapsulated electronic hearing aid components defining a soft structure after removal of the shell that directly contacts the ear canal, compliant to the user's ear canal during use, and substantially solid so that it is free of void spaces between the electronic hearing aid components and the ear canal;
   e) the combination of the soft compliant structure and the encapsulated electronic hearing aid components enabling a precise representation of the user's ear canal, flexing with jaw motion, and a cushioning of the interface between the user's ear canal and the electronic hearing aid components; and
   f) wherein the soft polymeric body has a Durometer Hardness, Shore A, of less than about 40 points.

2. The hearing aid molding apparatus of claim 1 wherein the soft polymeric outer shell is of a silicone material.

3. The hearing aid molding apparatus of claim 1 wherein the mounting member includes an acrylic portion.

4. The hearing aid molding apparatus of claim 1 wherein the soft polymeric filler is a silicone material.

5. The hearing aid molding apparatus of claim 1 wherein the soft polymeric filler is a silicone material having a hardness of between about 3 and 55 Durometer Shore A.

6. The hearing aid molding apparatus of claim 1 wherein the hollow outer shell is a mold member that defines a cavity with the mounting member that is filled with the soft polymeric filler.

7. The hearing aid molding apparatus of claim 1 wherein the encapsulated electronic hearing aid components include a receiver.

8. The hearing aid molding apparatus of claim 1 wherein the encapsulated electronic hearing aid components include a receiver and a receiver tube.

9. The hearing aid molding apparatus of claim 1 wherein the encapsulated hearing aid components include one or more components that are positioned next to the isthmus of the user's ear canal during use.

10. The hearing aid molding apparatus of claim 1 wherein the encapsulated electronic hearing aid components include one or more components that are positioned to direct amplified sound to the tympanic membrane of the user's ear during use.

11. A hearing aid molding apparatus for constructing a hearing aid that is to be contained in a user's ear comprising:
   a) a mounting plate having a medial side and a lateral side, the medial side providing a support surface;
   b) a plurality of electronic hearing aid components supported by the mounting plate;
   c) a soft polymeric hollow outer shell that is joined to the mounting plate, the outer shell and mounting plate defining a mold cavity that contains the plurality of electronic hearing aid components and that can be filled with a soft polymeric filler material;
   d) the soft polymeric filler substantially fills the mold cavity, the outer shell being removable from the soft polymeric filler to form a soft polymeric body that engages the inner respective surfaces of the mounting member to thereby minimize the volume of void space and encapsulate the plurality of electronic hearing aid components, the soft polymeric body having an inner surface shaped to conform to and that contacts the ear canal of a user;
   e) the soft polymeric body and the encapsulated electronic hearing aid components defining a soft structure compliant to the ear canal during use, and substantially solid so that it is free of void spaces between the plurality of electronic hearing aid components and the ear canal;
   f) the combination of the soft compliant structure and the encapsulated electronic hearing aid components enabling a precise representation of the user's ear canal, flexing with jaw motion, and a cushioning of the interface between ear canal and plurality of electronic hearing aid components; and g) wherein the soft polymeric body has a Durometer Hardness, Shore A, of less than about 40 points.

12. The hearing aid molding apparatus of claim 11 wherein the mounting plate is acrylic.

13. The hearing aid molding apparatus of claim 11 wherein the mounting plate is generally circular.

14. The hearing aid molding apparatus of claim 11 wherein the mounting plate supports the plurality electronic hearing aid components on both the medial and lateral side thereof.

15. The hearing aid molding apparatus of claim 11 further comprising a layer that enhances bonding between the mounting plate and the soft polymeric filler.

16. The hearing aid molding apparatus of claim 11 further comprising a layer affixed to the lateral surface of the mounting plate that enhances bonding between the mounting plate and the soft polymeric filler.

17. The hearing aid molding apparatus of claim 11 further comprising a temporary removable seal that affixes the hollow outer shell to the mounting plate.

18. The hearing aid molding apparatus of claim 11 wherein the mounting plate is much harder than the soft polymeric filler.

19. The hearing aid molding apparatus of claim 11 wherein both the medial and lateral side of the mounting plate support electronic hearing aid components.

20. A hearing aid molding apparatus for constructing a hearing aid that is contained in the ear comprising:
   a) a form that fills a user's ear canal to accurately define the shape of the user's ear canal;
   b) a mounting member providing a support for holding one or more electronic hearing aid components mounted thereto;
   c) a soft polymeric hollow outer shell that is only temporarily joined to the mounting member, the outer shell having an inner surface that conforms to the outer surface of the form so that the inner surface of the outer shell accurately defines the shape of the user's ear canal;
   d) the outer shell and mounting member defining a mold cavity that contains a plurality of electronic hearing aid components and that can be filled with a soft polymeric filler material;
   e) the soft polymeric filler substantially fills the mold cavity, the outer shell being removable from the soft polymeric filler to form a soft polymeric body that engages the inner respective surfaces of the mounting member to thereby minimize the volume of void space and encapsulate the plurality of electronic hearing aid components, the soft polymeric body having an inner surface shaped to conform to and that contacts the ear canal of a user;
   f) the soft polymeric body and the encapsulated electronic hearing aid components defining a soft structure compliant to the ear canal during use, and substantially solid so that it is free of void spaces between the plurality of electronic components and the ear canal;
   g) the combination of the soft compliant structure and the encapsulated plurality of electronic hearing aid components enabling a precise representation of the user's ear canal, flexing with jaw motion, and a cushioning of the interface between ear canal and the plurality of electronic hearing aid components; and
   h) wherein the soft polymeric body has a Durometer Hardness, Shore A, of less than about 40 points.

21. The apparatus of claim 20, wherein the hearing aid is sized to fit completely in the ear canal of the user.

22. The apparatus of claim 1, wherein the hearing aid is sized to fit completely in the ear canal of the user.

23. The apparatus of claim 11, wherein the hearing aid is sized to fit completely in the ear canal of the user.

* * * * *